(12) United States Patent
Azuma et al.

(10) Patent No.: US 8,361,966 B2
(45) Date of Patent: Jan. 29, 2013

(54) USE OF INTERLEUKIN-11 AS THERAPEUTIC AGENT FOR HEART DISEASE

(75) Inventors: Junichi Azuma, Suita (JP); Yasushi Fujio, Suita (JP); Ryusuke Kimura, Suita (JP); Makiko Maeda, Suita (JP); Atsushi Arita, Suita (JP); Masanori Obana, Suita (JP); Takashi Ito, Suita (JP); Tsuyoshi Fukuda, Suita (JP)

(73) Assignee: Osaka University, Osaka (JP)

( * ) Notice: Subject to any disclaimer, the term of this patent is extended or adjusted under 35 U.S.C. 154(b) by 560 days.

(21) Appl. No.: 12/312,077

(22) PCT Filed: Oct. 24, 2007

(86) PCT No.: PCT/JP2007/070699
§ 371 (c)(1),
(2), (4) Date: Dec. 4, 2009

(87) PCT Pub. No.: WO2008/050789
PCT Pub. Date: May 2, 2008

(65) Prior Publication Data
US 2010/0093976 A1 Apr. 15, 2010

(30) Foreign Application Priority Data
Oct. 27, 2006 (JP) .................................. 2006-293062

(51) Int. Cl.
*A61K 38/20* (2006.01)
*C07K 14/54* (2006.01)
(52) U.S. Cl. ........................................ 514/16.4; 530/351
(58) Field of Classification Search ........................ None
See application file for complete search history.

(56) References Cited

U.S. PATENT DOCUMENTS

| | | | |
|---|---|---|---|
| 5,679,339 A | 10/1997 | Keith et al. | |
| 5,948,402 A | 9/1999 | Keith et al. | |
| 5,958,401 A | 9/1999 | Keith et al. | |
| 6,126,933 A | 10/2000 | Warne et al. | |
| 6,270,759 B1 | 8/2001 | Keith et al. | |
| 6,274,135 B1 | 8/2001 | Keith et al. | |
| 6,887,461 B1 | 5/2005 | Warne et al. | |
| 7,220,407 B2 * | 5/2007 | Mehta et al. | 424/85.1 |
| 7,252,973 B1 * | 8/2007 | Goto et al. | 435/70.1 |
| 2003/0147849 A1 | 8/2003 | Warne et al. | |
| 2005/0129658 A1 | 6/2005 | Warne et al. | |

FOREIGN PATENT DOCUMENTS

| | | |
|---|---|---|
| JP | 11-508556 | 7/1999 |
| WO | 97/01353 | 1/1997 |

OTHER PUBLICATIONS

Alfonso-Jaume et al., Am J Physiol Heart Circ Physiol 291: H1838-H1846, May 2006.*
K. A. Kuenzler et al., "IL-11 Pretreatment Reduces Cell Death after Intestinal Ischemia-Reperfusion", Journal of Surgical Research, vol. 108, No. 2, pp. 268-272, 2002.
C. Ancey et al., "Secretion of IL-6, IL-11 and Lif by Human Cardiomyocytes in Primary Culture", Cytokine, vol. 18, No. 4, pp. 199-205, May 21, 2002.
Y. Zou et al., "Leukemia Inhibitory Factor Enhances Survival of Cardiomyocytes and Induces Regeneration of Myocardium after Myocardial Infarction", Circulation, vol. 108, pp. 748-753, 2003.
K. C. Wollert et al., "Cardiotrophin-1 Activates a Distinct Form of Cardiac Muscle Cell Hypertrophy", The Journal of Biological Chemistry, vol. 271, No. 16, pp. 9535-9545, Apr. 19, 1996.
R. A. Gadient et al., "Leukemia Inhibitory Factor, Interleukin 6, and Other Cytokines Using the GP130 Transducing Receptor: Roles in Inflammation and Injury", Stem Cells, vol. 17, pp. 127-137, 1999.
T. Taga et al., "GP130 and the Interleukin-6 Family of Cytokines," Annu. Rev. Immunol., vol. 15, pp. 797-819, 1997.
W. L. Trepicchio et al., "Interleukin-11, A GP130 Cytokine", Annals New York Academy of Sciences, vol. 856, pp. 12-21, 1998.
W. L. Trepicchio et al., "Recombinant Human IL-11 Attenuates the Inflammatory Response Through Down-Regulation of Proinflammatory Cytokine Release and Nitric Oxide Production", The Journal of Immunology, vol. 157, pp. 3627-3634, 1996.
M. S. Gordon et al., "A Phase I Trial of Recombinant Human Interleukin-11 (Neumega rhIL-11 Growth Factor) in Women with Breast Cancer Receiving Chemotherapy", Blood, vol. 87, No. 9, pp. 3615-3624, May 1, 1996.
Gan To Kagaku Ryoho, Japan J. Cancer Chemother, vol. 32, No. 4, pp. 489-496, Apr. 2005 with English abstract.
Gan To Kagaku Ryoho, Japan J. Cancer Chemother, vol. 32, No. 4, pp. 479-487, Apr. 2005 with English abstract.

* cited by examiner

*Primary Examiner* — Marianne P Allen
(74) *Attorney, Agent, or Firm* — Wenderoth, Lind & Ponack, L.L.P.

(57) ABSTRACT

The present invention demonstrates the myocardial protective effects of interleukin 11 in vivo, and provides preventive, therapeutic, or other types of drugs for heart disease using interleukin 11 as the active ingredient. The present invention, by utilizing the myocardial protective effects of interleukin 11, can suppress the progress of myocardial injury, prevent the onset of heart failure, or suppress the progress of heart failure.

3 Claims, 7 Drawing Sheets

(a)

(b)

n=151-227 Mean±SD, *: $p<0.05$ (c)

n=151-227 Mean±SD, *: $p<0.05$ (a)

(b)

Mean±SD, *:$p<0.05$ (a)

(b)

Infarct area : THE AREA OF FIBROTIC REGION WITH RESPECT TO THE AREA OF THE LEFT VENTRICULAR MYOCARDIUM

USE OF INTERLEUKIN-11 AS THERAPEUTIC AGENT FOR HEART DISEASE

This application is a U.S. national stage of International Application No. PCT/JP2007/070699 filed Oct. 24, 2007.

TECHNICAL FIELD

The present invention relates to a use of interleukin 11 as a therapeutic agent for heart disorders, particularly in finding novel efficacy of interleukin 11 based on its myocardial protective effects found in vitro and in vivo, and to a use of interleukin 11 as a preventive or therapeutic drug for heart diseases.

BACKGROUND ART

Cytokines are known to play important roles in maintaining the homeostasis of cardiac muscle. In particular, leukemia inhibitory factor (LIF), an interleukin 6 (IL-6) family cytokine, is reported to have a role in the signal transduction into cardiac cells via the gp130 (glycoprotein 130)/JAK pathway, providing various effects such as heart protection, angiogenesis, and hypertrophy of cardiomyocytes (Non-Patent Documents 1 and 2). However, because LIF strongly induces inflammation (Non-Patent Document 3), a cytokine therapy for cardiovascular disease using LIF is generally considered difficult. Specifically, the use of LIF in drug applications is considered impractical because of its side effects such as fever.

In addition to LIF, the IL-6 cytokine family includes IL-6, cardiotrophin-1, oncostatin M, and interleukin 11 (hereinafter, also referred to as "IL-11"). All of these cytokines are known to activate the downstream signal transduction system through binding to their specific α receptors and to the common β chain gp130 (Non-Patent Document 4). While these cytokines share the same signaling pathways, and are functionally redundant, they also show completely different effects, as reported in Non-Patent Document 5. By probing for myocardial cytokines that share the same signal transduction system with LIF but are less inflammatory, it would be possible to establish a novel cytokine therapy for cardiovascular disease.

The effects of IL-11 as an anti-inflammatory cytokine have been reported (Non-Patent Document 6). Further, IL-11, a platelet growth factor, has been approved in the United States as a therapeutic agent for thrombocytopenia in cancer chemotherapy, and the efficacy and safety of IL-11 has been reported (Non-Patent Document 7). In Japan, clinical trials are underway for thrombocytopenia in cancer chemotherapy, and certain information is available concerning the safety of IL-11 (Non-Patent Documents 8 and 9). However, the effects of IL-11 on the cardiovascular system have not been fully studied, and no efforts have been made concerning the application of IL-11 to cardiovascular disease.

In Patent Document 1, IL-11 is described as having anti-inflammatory effects, and therefore being effective for various disorders including reperfusion injury after myocardial infarction. However, the publication does not include any example that actually demonstrates the efficacy of IL-11 in reperfusion injury after myocardial infarction, and it is unclear whether IL-11 actually has therapeutic effects on heart diseases.

Non-Patent Document 1: Circulation. 2003; 108:748-753.
Non-Patent Document 2: J Biol Chem. 1996; 271:9535-45.
Non-Patent Document 3: Stem Cells. 1999; 17:127-37.
Non-Patent Document 4: Annu Rev Immunol. 1997; 15:797-819.
Non-Patent Document 5: Ann. N.Y. Acad. Sci. 1998; 856: 12-21.
Non-Patent Document 6: J. Immunol. 1996; 157:3627-3634.
Non-Patent Document 7: Blood. 1996; 87:3615-3624.
Non-Patent Document 8: Gan To Kagaku Ryoho. 2005; 32:489-96.
Non-Patent Document 9: Gan To Kagaku Ryoho. 2005; 32:479-87.
Patent Document 1: JP-T-11-508556

DISCLOSURE OF THE INVENTION

Technical Problem

There is an ongoing demand for the establishment of an effective treatment of heart diseases using a new drug. For example, heart failure is treated with drugs such as ACE inhibitors (angiotensin converting enzyme inhibitors), β blocker, diuretics, and ARBs (angiotensin II receptor blockers). However, the effects of these drugs are insufficient, and the prognosis is poor. These drugs block the signals of the neurohumoral factors associated with myocardial injury. Considering the vast amounts of medical expenses spent on the treatment of heart failure each year in Japan and globally, it would be highly beneficial to develop a new drug intended to prevent the onset of heart failure or establish a treatment for heart failure.

The present invention was made under these circumstances, and an object of the invention is to provide preventive, therapeutic, or other types of drugs for heart diseases using interleukin 11 as the active ingredient, based on studies of the applicability of interleukin 11 as a therapeutic agent for cardiovascular diseases.

Technical Solution

As described above, interleukin 11 (IL-11), currently in use in other medical applications (therapeutic drug for thrombocytopenia), is a member of the IL-6 class cytokines that elicit little inflammatory response. Considering the aforementioned circumstances, the applicability of IL-11 for the prevention or treatment of heart diseases was investigated. The study revealed various effects of the direct action on cardiomyocytes and the heart. It was also found that IL-11, in vivo, (1) is useful in the protection of cardiac muscle against ischemia/reperfusion, (2) enhances expression of the vascular endothelial growth factor in cardiomyocytes and promotes myocardial angiogenesis, and (3) is effective in the repair and regeneration of tissues even when administered after myocardial tissue injury. The present invention was completed based on these and other findings.

Specifically, the present invention demonstrates the myocardial protective effects of interleukin 11 in vivo, and provides a preventive or a therapeutic drug for heart diseases using interleukin 11 as the active ingredient. The present invention, utilizing the myocardial protective effects of interleukin 11, can inhibit the progress of myocardial injury, prevent the onset of heart failure, and inhibit the progress of heart failure.

The inventors of the present invention studied the effects of IL-11 on cardiomyocytes and the heart both in vitro and in vivo. The study elucidated various actions of IL-11 on cardiomyocytes and the heart, as described below.

First, IL-11 receptors were found to be expressed in cardiomyocytes and the heart (FIG. 1). This suggests that the myocardial tissue is the immediate target of IL-11 in vivo, providing evidence that IL-11 directly acts on the myocardial tissue.

Next, cultured cardiomyocytes were treated with IL-11, and activation (phosphorylation) of the downstream signal transducers, such as STAT3 and ERK1/2, was analyzed in order to study the effects of IL-11 on the signal transduction system in heart. The results confirmed the quick activation of STAT3 and ERK1/2 in cardiomyocytes treated with IL-11 (FIG. 2 and FIG. 3). Further, submaximal activation was observed at the IL-11 concentration of 20 ng/ml (FIG. 4), which demonstrates the signal transducing ability of IL-11 for the cardiac muscle near this physiological concentration.

The study also found that IL-11 greatly increases the area of cultured cardiomyocytes (FIG. 5), and enhances the viability (survival) of cardiomyocytes (FIG. 6). The increase in area is due to an extension along the long axis of the cell. Considering the reported involvement of the gp130-mediated activation pathway of the ERK family in the hypertrophy of cardiomyocytes, IL-11 signal transduction is believed to be mediated by ERK. Further, the result of an MTS assay confirmed that IL-11 enhances the viability (survival) of cardiomyocytes, showing that IL-11 indeed acts, in vitro, to protect cardiomyocytes from damage caused in serum-free cardiomyocyte culture.

The observation that IL-11 activates STAT3 in cultured cardiomyocytes raised the possibility that IL-11 might also activate STAT3 in vivo in the heart and increase capillary density. To test this, the effects of repeated administration of IL-11 on the capillary density were examined in the heart. The capillary density increased nearly 1.2 fold on average in mice treated with IL-11, compared with a control group (FIG. 7), showing that IL-11 acts to promote vascular formation in vivo.

Since the increased capillary density induced by STAT3 activation was thought to involve increased expression of VEGF (vascular endothelial growth factor; a regulatory factor of vascular formation), the influence of the IL-11 treatment on VEGF mRNA expression level was examined in cultured cardiomyocytes. The results showed that IL-11 indeed enhances VEGF mRNA expression (FIG. 8). Because a STAT3 regulatory site is identified in a VEGF promoter, the induction of VEGF expression through STAT3 activation appears to play an important role in increasing the capillary density following repeated administration of IL-11.

With these findings, studies using murine ischemia/reperfusion model were conducted to show that preadministration of IL-11 reduces myocardial ischemia/reperfusion injury, or more specifically, suppresses post-reperfusion myocardial infarction and protects the heart, as follows.

Mice were preadministered with 200 ng of IL-11 through the tail vein. After 18 hours, the chest was opened, and the left coronary artery was ligated to induce ischemia. After one hour of an ischemic episode followed by one hour of reperfusion, the infarct region in the cardiac muscle was assessed using TTC (triphenyltetrazolium chloride) staining. The result showed about a 60% reduction in infarct size in the IL-11 administered group, compared with the control (FIG. 9).

IL-11 also had a myocardial protective effect when administered after myocardial injury, demonstrating that IL-11 is also effective in tissue repair and regeneration (FIG. 10). Further, intravenous injection of IL-11 in mice quickly induced expressions of the reactive oxygen species scavenger metallothionein (MT-1, MT-2), and the cell protection factor SPRR (small proline rich repeated protein) in the heart (FIG. 11), promoting activation of these molecules in the heart.

Further analyses revealed that IL-11 administration in mice after myocardial injury improves the survival rate, confirming IL-11's ability to improve survival after myocardial infarction (FIG. 12), and that IL-11 represses (inhibits) the expression of inflammatory cytokines after myocardial infarction to provide anti-inflammatory effects in infarct tissue (FIG. 13).

As noted above, IL-11 has myocardial protective effects both in vitro and in vivo, demonstrating the effect of IL-11 to suppress ischemia/reperfusion injury. Ischemia/reperfusion injury is a cardiac muscle injury caused by reactive oxygen generated in the cardiac muscle, and is believed to share a common mechanism with various other myocardial injuries. Accordingly, a preventive or a therapeutic drug for heart disease using IL-11 as the active ingredient according to the present invention is effective not only for ischemia/reperfusion injury, but for a wide range of other heart diseases, such as a myocardial disorder (myocardial damage), cardiovascular disease, heart failure, and ischemic heart diseases (including angina and myocardial infarction).

Further, with the novel effects of IL-11 on cardiomyocytes and the heart as elucidated by the foregoing analyses, the present invention provides not only a preventive or therapeutic drug for heart disease, but also myocardial protective agents, survival enhancers for cardiomyocytes, cardiovascular angiogenic stimulators, activation stimulators or expression enhancers for reactive oxygen species scavengers and cell protection factors in the heart; and all use IL-11 as the active ingredient. As used herein, the "myocardial protective agents" refer to myocardial remodeling inhibitors, or myocardial repair/regeneration stimulators against myocardial insult. The "myocardial remodeling inhibitors" refer to drugs that inhibit the cardiac muscle from responding to injuries by undergoing, for example, fibrosis, which is detrimental to sustaining the heart function over a long time period (myocardial remodeling). Accordingly, the drugs promote recovery or regeneration from injury, thereby allowing the cardiac muscle functions to be sustained.

Exemplary use of a drug of the present invention is described below. A drug of the present invention is administrable to humans (or animals) as a pharmaceutical composition prepared either directly from the active ingredient interleukin 11 (IL-11), analogs, derivatives, or modified forms thereof, or together with a base (vehicle) or a common pharmaceutical preparation carrier. The form of administration of the pharmaceutical composition is not particularly limited, and may be suitably selected according to use. For example, the dosage form may be an oral form, such as a tablet, a capsule formulation, a granule, a subtle granule, or a powder, or a parenteral form such as an injection, a suppository, or an embrocation. The administration method is preferably parenteral administration. Other examples include intravenous injection, subcutaneous injection, nasal administration, and direct administration to the heart.

The oral form such as a tablet, a capsule formulation, a granule, a subtle granule, or a powder can be produced by an ordinary method using, for example, starch, lactose, sucrose, trehalose, mannite, carboxymethylcellulose, cornstarch, and inorganic salts. The IL-11 content in the preparation is not particularly limited, and may be suitably set. The preparation of this form may suitably include additives such as a binder, a disintegrant, a surfactant, a lubricant, a fluidity promoting agent, a flavoring agent, a colorant, and a fragrance.

In a parenteral form, the dose is adjusted according to such factors as the age, body weight, and the extent of disease of a patient. For example, a dose is given either systemically or locally by intravenous injection, intravenous drip injection, subcutaneous injection, nasal administration, intraperitoneal administration, intramuscular injection, or direct administration to the heart. An appropriate parenteral dose of IL-11 needed to obtain the desirable effects of the present invention is generally about 8 μg/kg body weight per day for adults, though it depends on factors such as the age, body weight, and the extent of the disease of a patient, as noted above. The parenteral form can be produced by an ordinary method, and a diluent, such as distilled water for injection, and physiological saline, may generally be used. Further, a disinfectant, an antiseptic, or a stabilizer may be added as required. For stability, the parenteral form may be readjusted in the form of a liquid preparation immediately before use, from a lyophilized material prepared by freezing the preparation in a container such as a vial, and removing water therefrom using an ordinary lyophilization technique. Further, an isotonic agent, a stabilizer, an antiseptic, or a soothing agent may be added, as required. The IL-11 content in the preparation is not particularly limited, and may be suitably set. Other examples of the parenteral form include embrocations such as a topical liquid and an ointment, and a suppository for intrarectal administration. These can be produced by an ordinary method.

It is also possible to deliver the drug into the body using a known DDS (drug delivery system), for example, by encapsulating IL-11 or an IL-11-encoding gene expression vector in a carrier such as a liposome.

For applications intended to prevent the onset of heart diseases, IL-11 may be used as a raw material of food (food compositions) such as functional foods and supplements to develop food that has a heart disease preventative effect. Specifically, IL-11 may be added as a raw material of various drinks and processed foods, or processed into a pellet, a tablet, a granule etc. with an additional component such as an excipient (for example, dextrin, lactose, or starch), a fragrance, or a dye, or into a capsule by being coated with gelatin or other materials. In this way, IL-11 can be used to provide food, such as health foods and food supplements that have an effect of heart disease prevention.

As described above, the present invention protects myocardial tissue using IL-11. Most conventional drugs having myocardial protective effect work by blocking signals of the neurohumoral factor associated with myocardial injury. In contrast, the present invention uses IL-11 to activate cardioprotection/angiogenic signals.

Other features of a drug of the present invention are as follows.

(1) The direct or indirect target of the drug is a variety of cells constituting the myocardial tissue, such as cardiomyocytes, vascular endothelial cells, myocardial tissue stem cells, and myocardial tissue fibroblasts.

(2) The drug does not control the inflammatory response after the myocardial tissue damage, but acts to prevent the myocardial tissue damage itself that causes an inflammatory response.

(3) IL-11 is used to modulate myocardial tissue repair and/or regeneration such as cell protection, angiogenesis, and vascular development during the process of tissue repair after myocardial tissue injury.

(4) A drug of the present invention is expected to remain effective over extended time periods during the tissue repair and/or regeneration process, such as promoting vascular formation and differentiation induction of myocardial tissue stem cells, which continues several days to several weeks after the injury. Thus, the drug is also expected to have a long lasting effect, for example, in the prevention of the onset of heart failure following myocardial infarction.

Figure 12:
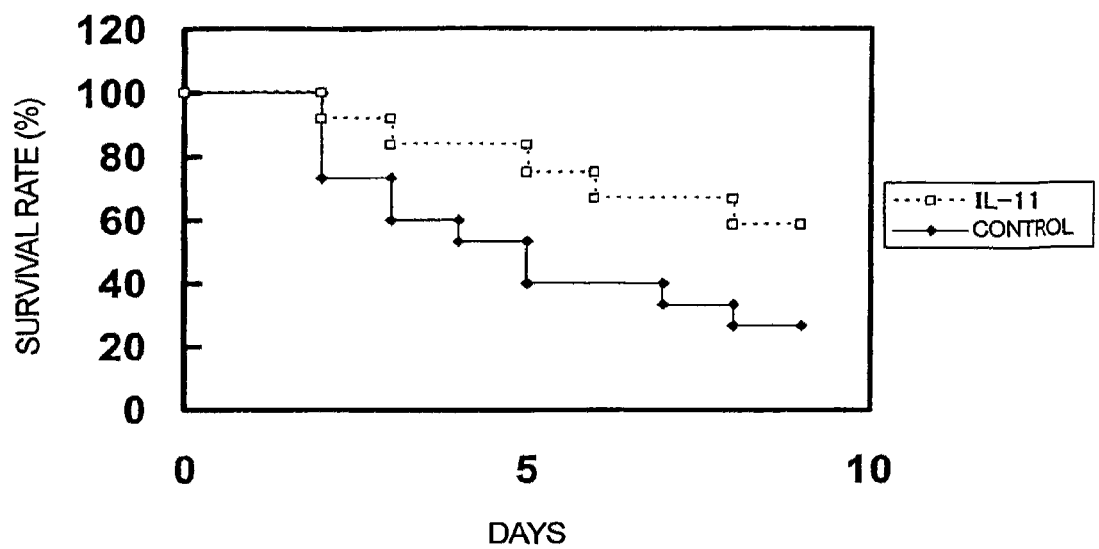

FIG. 12 is a graph presenting the survival curves of IL-11-treated mice after exposure to myocardial infarction by ligating the coronary artery, and a control group (PBS-administered group); n=15 for the control group; n=12 for the IL-11 administered group.

Figure 13:
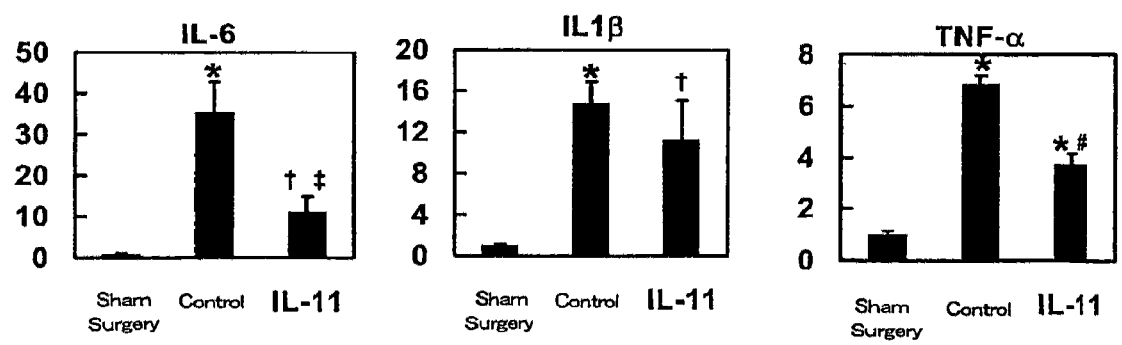

FIG. 13 is a graph presenting the effects of IL-11 administration on the expression level of various cytokines (IL-6, IL-1β, and TNF-α) in the infarct tissue, using myocardial infarcted mice; n=7 for the sham surgery group; n=6 for the control (PBS-administered) group; n=6 for the IL-11 administered group; the vertical axis, relative values; † and *, statistical significance against the sham surgery group; ‡ and #, statistical significance against the control group.

EXAMPLES

The following will describe examples of the present invention with reference to the accompanying drawings. It should be noted, however, that the invention is in no way limited by the descriptions below.

1. Methods

Rat Neonatal Cardiomyocyte Culture

Rat neonatal cardiomyocytes were cultured according to the method of Kunisada et al. (Circulation. 1996; 94:2626-2632). Specifically, a heart removed from a day old Wistar rat was dissociated into single cells by treatment with a degrading enzyme solution (20 mM HEPES, 130 mM NaCl, 3 mM KCl, 1 mM $NaH_2PO_4.2H_2O$, 4 mM glucose, 3.3 µM phenol red, 0.1% collagenase type IV, 0.1% trypsin, 30 µg/ml DNase I). The cardiomyocytes were separated by taking advantage of the time difference in cell adhesion onto the dish. The cells were cultured using Dalbecco's modified Eagle's medium/Ham F12 (DMEM/HamF12) containing 5% neonatal calf serum (NCS) and 0.1 µg/ml Bromodeoxyuridine (BrdU). It has been confirmed that cardiomyocytes of 95% or more purity can be obtained by this method, using immunostaining with anti-sarcomeric α-actinin antibody.

The IL-11 and LIF used in the addition experiment were purchased from PeproTech and Chemicon International, respectively.

Immunostaining and Morphology Observation

After stimulating the cardiomyocytes with cytokine, the medium was removed by aspiration, and the cells were washed twice with PBS(−). Then, the cells were fixed with 3.7% formaldehyde for 10 minutes, and treated with 0.2% Triton X-100 in PBS(−) for 2 minutes. After washing with PBS(−), the cells were allowed to react with anti-sarcomeric α-actinin antibody (1:100; SIGMA; primary antibody) at room temperature for 30 minutes. This was followed by a reaction with Alexa 488-conjugated goat anti-mouse IgG (1:200; Molecular Probe; secondary antibody) at room temperature for 30 minutes. After the reaction, the morphology of the cardiomyocytes was observed with a fluorescent microscope (IX70; OLYMPUS), and images were taken. The cell images were processed with ImageJ (NIH) to measure the area, width, and length of the cells. The parameters used to quantify cell morphology are as defined in the method of Wollert et al. (J Biol Chem. 1996; 271:9535-45).

Western Blotting

Western blotting was performed according to the method of Nakaoka et al. (Circ. Res. 2003; 93:221-229). The cardiomyocytes were stimulated with cytokine, and washed twice with PBS(−). Then, the cells were dissolved in SDS-sample buffer (62.5 mM Tris-HCl, pH6.8; 10% glycerol; 2% SDS; 0.001% bromophenol blue; 5% 2-mercaptoethanol), collected, and heat denatured at 95° C. for 5 minutes before being preserved at −80° C.

The sample was separated on an SDS-polyacrylamide gel, and transferred to a PVDF membrane (Millipore). The PVDF membrane was blocked with 2% skimmed milk. As the primary antibodies, anti-phospho-STAT3 antibody (Cell Signaling Technology) and anti-phospho-ERK1/2 antibody (Cell Signaling Technology) (1:500) were used. Horseradish peroxidase (HRP)-labeled rabbit IgG antibody (Santa Cruz Biotechnology) (1:5000) was used as the secondary antibody. After the reaction, signals were detected on an X-ray film using Chemi-Lumi One (Nacalai Tesque). For image analysis, a Scion Image (Scion Corporation) was used. To quantify the extent of phosphorylation, the total proteins were detected with anti-STAT3 antibody (Santa Cruz Biotechnology) and anti-ERK1/2 antibody (Cell Signaling Technology), and used to correct the phosphorylated protein bands.

RT-PCRS

Total RNA was prepared according to the acid guanidinium thiocyanate-phenol-chloroform method (Anal. Biochem. 1987; 162:156-159). Specifically, the cells were dissolved in QIAzol™ (QIAGEN), and the total RNA was extracted according to the attached protocol. The total RNA so extracted was dissolved in RNase-free water, and the concentration was measured using an absorptiometer. Purity was also confirmed from a ratio of absorbances at 260 nm and 280 nm. The RNA sample was preserved at −80° C. until the PCR reaction was performed.

For the detection of IL-11 receptor mRNA expression by RT-PCR, the following primers were used.

```
Forward: 5'-GTGTCCTGGTTTCGGGATGG-3' (SEQ ID NO: 1)

Reverse: 5'-TCCAGGTGCCAGCATCCAGA-3' (SEQ ID NO: 2)
```

For the reverse transcription reaction, 1 µg of total RNA was used as the template, and 20 µl of an RT reaction mixture containing 0.5 µg of oligo $(dT)_{12-18}$ primer (Invitrogen), dNTP (0.5 mM each), 40 units of RNase Inhibitor (TOYOBO), and 100 units of ReverTra Ace (TOYOBO) was used. The reaction was performed at a cycle consisting of 42° C. for 55 minutes, and 70° C. for 15 minutes to synthesize cDNA. After the reaction, sterile distilled water was added to adjust the volume to 40 µl. PCR for the IL-11 receptor used 0.5 µl of the cDNA solution as the template in a 25 µl total volume containing the primers (0.2 µM each), dNTP (0.2 mM each), 2U AmpliTaq Gold DNA polymerase (Applied Biosystems), and 2.5 µl of 10×PCR Buffer (containing 100 mM Tris-HCl, pH 8.3; 500 mM KCl; 15 mM $MgCl_2$). The reaction was performed first by heating at 94° C. for 10 minutes, and performing 35 cycles consisting of heat denaturing at 94° C. for 30 seconds, annealing at 60° C. for 30 seconds, and extension reaction at 72° C. for 1 minute, followed by extension reaction at 72° C. for 7 minutes.

The PCR product was electrophoresed on 2% agarose gel, and the resulting bands were detected using a UV transilluminator after ethidium bromide staining.

The VEGF mRNA quantification method using Real-time RT-PCR is described below. The quantification of VEGF mRNA was performed using a TaqMan™ Assay on Demand reagents (Assay ID; Rn00582935_m1, Applied Biosystems). The reaction was performed using 500 ng of total RNA as the template, and a reaction mixture containing 12.5 µl of 2× THERMOSCRIPT Reaction Mix, 0.5 µl of THERMOSCRIPT PLUS/PLATINUM Taq MIX, 20 units of RNase Inhibitor (TOYOBO), 0.25 µl of ROX Reference Dye (Invitrogen), and 1 µl of TaqMan™ Assay on Demand reagents. The total volume was adjusted to 25 µl with RNase-free water. As the internal standard of quantification, β-actin was used. In the measurement system for β-actin (25 µl), the final concentration was 300 nM for the primers, and 500 nM for the probe. The total RNA, 2× THERMOSCRIPT Reaction Mix, THERMOSCRIPT PLUS/PLATINUM Taq MIX, RNase Inhibitor, and ROX Reference Dye were used in the same amounts as in the quantification of VEGF mRNA. The reaction followed the procedures of the PLATINUM™ Quantitative RT-PCR THERMOSCRIPT™ One-Step System (Invitrogen) according to the attached protocol. The sequences of the primer set for the β-actin, and the probe sequence are as follows.

```
Forward primer:
                                        (SEQ ID NO: 3)
5'-GACAGGATGCAGAAGGAGATTACTG-3'

Reverse primer:
                                        (SEQ ID NO: 4)
5'-AGAGCCACCAATCCACACAGA-3'

Probe:
                                        (SEQ ID NO: 5)
5'-(FAM)-AAGATCATTGCTCCTCCTGAGCGCAAGTA-(TAMRA)-3'
```

Cell Viability Assay

A cell viability assay was performed according to the method of Fujio et al. (Circulation. 2000; 101:660-667) with slight modifications. Cardiomyocytes were cultured in serum-free medium with or without IL-11, and cell viability (survival) was evaluated with an MTS assay, which measures the metabolic activity for MTS. The MTS assay was performed using a commercially available kit (Promega).

Assessment of Myocardial Vascular Density

C57Bl/6 mice, 10 weeks of age, were repeatedly treated with IL-11 (8 µg/kg) or vehicle (PBS(−)) through the tail vein. The dose was given every four days for 5 weeks. The heart was removed, washed with PBS(−), and frozen in an O.C.T Compound (SAKURA™). The frozen sections (10 µm thick) were prepared with Cryostat (CM1850; LEICA). After air-drying, the sections were fixed with acetone, and used for immunohistochemical analysis.

The immunohistochemical analyses were performed using a Vectastain ABC kit (VECTOR LABORATORIES), according to the manufacturer's protocol. Anti-CD31 antibody (BD Biosciences) was used as the primary antibody, and the capillaries were stained with a DAB (3,3'-diamino benzidine tetrahydrochloride) substrate solution. The sample was examined with light microscopy, and capillaries were counted in number.

Production of Ischemia/Reperfusion Injury

Ischemia/reperfusion was produced in mice according to the method of Oshima et al. (Cardiovasc. Res. 2005; 65:428-435). IL-11 (8 µg/kg) or PBS(−) was intravenously administered 18 hours prior to surgery. C57Bl/6 mice (10 weeks of age) were intraperitoneally administered with Ketamine (Sankyo-Yell; 100 mg/kg) and xylazine (Bayer Medical Ltd.; 5 mg/kg). Under general anesthesia, the chest was opened with the mouse attached to a medical ventilator for laboratory animals (Shinano; 96 ml/min). With a surgical suture (7-0), the left anterior descending coronary artery was ligated to cause occlusion for 60 minutes, followed by 60-minute reperfusion. The episode of ischemia/reperfusion was confirmed by monitoring changes in ST-T on ECG. The body temperature of the mouse was maintained at 37° C. during the course of surgery. After one hour of reperfusion, the artery was ligated again, and 0.5 ml of a 4% Evans Blue (Sigma) PBS(−) solution was immediately injected into the left carotid artery to confirm the AAR (area at risk) of myocardial infarction. Then, the heart was immediately removed, and the infarct region was evaluated.

After excision, the heart was sliced to observe the short axial plane. The slice was immersed in a 2% triphenyltetrazolium chloride (TTC; Sigma) PBS(−) solution at 37° C. for 20 minutes. The area not stained with Evans Blue was measured as the AAR, and the percentage with respect to the left ventricle (left ventricular area; LVA) was calculated to evaluate the equivalence of the surgery. The area not stained with TTC and appearing white was measured as a myocardial infarct area (MIA), and the percentage with respect to AAR was calculated.

The coronary artery was ligated, and a myocardial infarction model was also created for an experiment in which IL-11 was administered after myocardial injury. Twenty-four hours after ligation, IL-11 was given daily for 5 days through the tail vein (only physiological saline (PBS) for the control). After about one month, the heart was removed from the mouse to assess myocardial fibrosis and intact cardiac muscle.

Semi-Quantitative RT-PCR Analysis

Semi-quantitative RT-PCR analysis was performed according to the method of Fujio et al. (J. Clin. Invest. 1997; 99:2898-2905). Total RNA was prepared according to the acid guanidinium thiocyanate-phenol-chloroform method. Using a reverse transcription reaction, cDNA was synthesized from 1 µg of total RNA, and PCR was performed using primers specific to the genes shown in Table 1 below. Confirmation of amplification products was made using 2% agarose gel electrophoresis.

TABLE 1

| Genes | Direction | Primer sequence |
|---|---|---|
| COX 2 | Forward | 5'-GGTCTGGTGCCTGGTCTGATGATGTATGC-3' (6) |
|  | Reverse | 5'-GGGGGTGCCAGTGATAGAGTGTGTTGAATT-3' (7) |
| INOS | Forward | 5'-TGAAGCCCCGCTACTACTCCATCA-3' (8) |
|  | Reverse | 5'-TTGCGGACCATCTCCTGCATTT-3' (9) |
| MT-1 | Forward | 5'-CGTAGCTCCAGCTTCACCAGATGTC-3' (10) |
|  | Reverse | 5'-TGGTGGCAGCGCTGTTCGT-3' (11) |
| MT-2 | Forward | 5'-ACCGATCTCTCGTCGATCTTCAA-3' (12) |
|  | Reverse | 5'-GCTTCTACATGGTCTATTTACACAGATGTG-3' (13) |
| SPRR1A | Forward | 5'-GGACCAAGTGCTATCTAACCATG-3' (14) |
|  | Reverse | 5'-GGTCTTCAGGCATGGCTCTGGAC-3' (15) |
| GAPDH | Forward | 5'-CATCACCATCTTCCAGGAGCG-3' (16) |
|  | Reverse | 5'-GAGGGGCCATCCACAGTCTTC-3' (17) |

Number in parentheses indicate sequence numbers of the sequence listing

Ethical Considerations for Animal Experimentation

The laboratory animals were used according to the animal experimentation guidelines of Osaka University.

Statistical Analysis

Student's t-test was used for the significance testing of the results. For analysis, Statcel (trade name) was used. The significance level was P<0.05.

2. Results

IL-11 Receptor is Expressed in Heart and Cardiac Muscle

Figure 1:
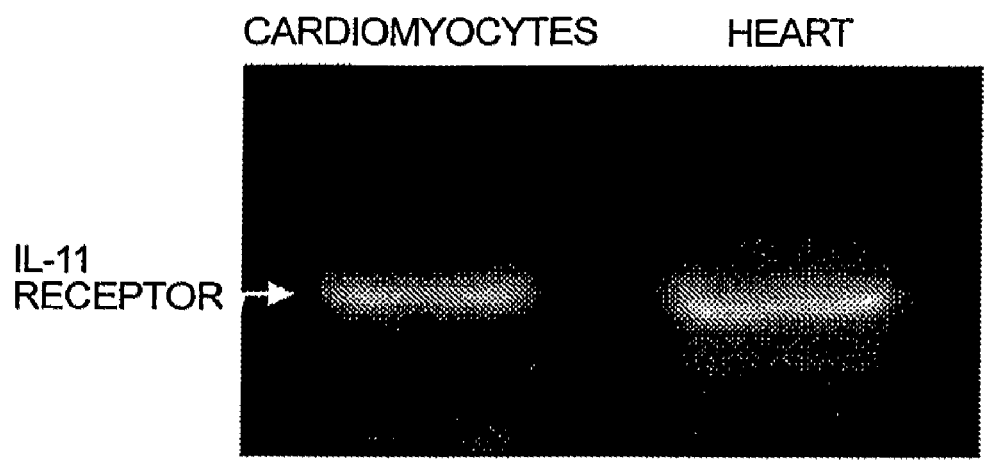
FIG. 1 presents the result of the RT-PCR analyses to examine IL-11 receptor mRNA expression, using total RNA prepared from cardiomyocytes and heart.

To address whether IL-11 receptor mRNA is expressed in cultured cardiomyocytes and the heart, RT-PCR was performed (FIG. 1). RT-PCR showed a band of 746 bp, indicating expression of IL-11 receptor mRNA in rat neonatal cultured cardiomyocytes and the mouse heart. No band was observed in the PCR reaction lacking the template. The PCR product obtained as above was excised, and its sequence was confirmed.

IL-11 Activates STAT3 and ERK1/2 in Cardiomyocytes

Figure 2:
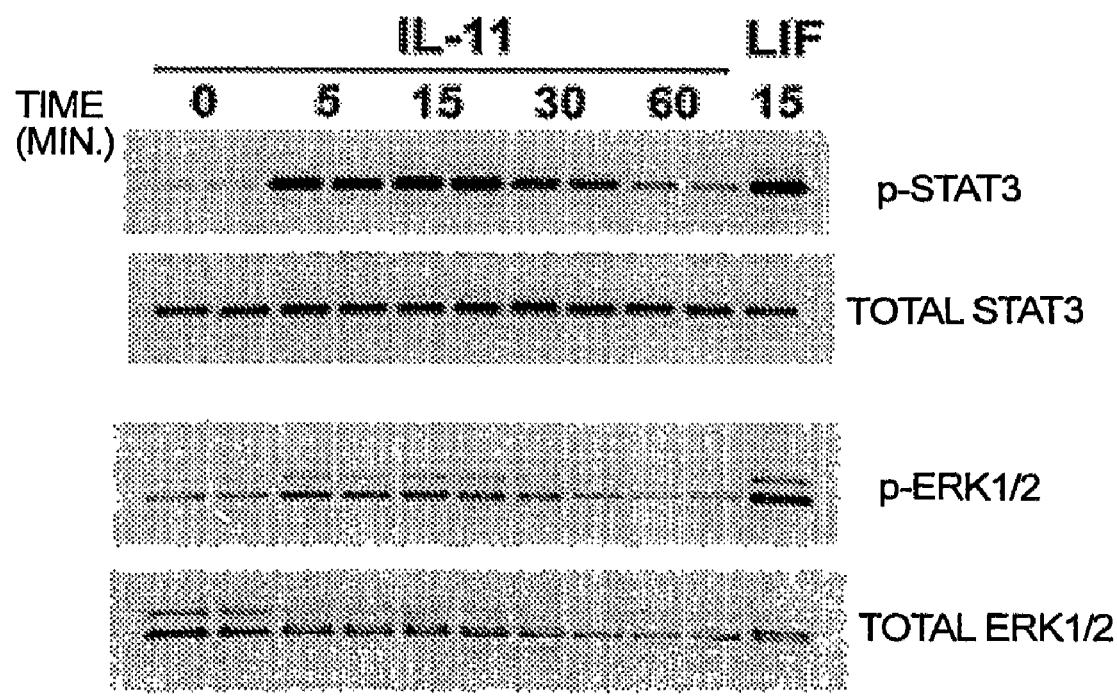
FIG. 2 presents the result of a Western blot analysis of STAT3 and ERK1/2 activation (phosphorylation) in response to IL-11 (20 ng/ml) stimulation in cultured cardiomyocytes; the result of LIF stimulation ($1\times10^3$ U/ml) is shown as a positive control.

Activation of STAT3 and ERK1/2 by IL-11 stimulation in cultured cardiomyocytes was analyzed by Western blotting. Phosphorylation of STAT3 and ERK1/2 was confirmed immediately after IL-11 treatment (FIG. 2).

Figure 3:
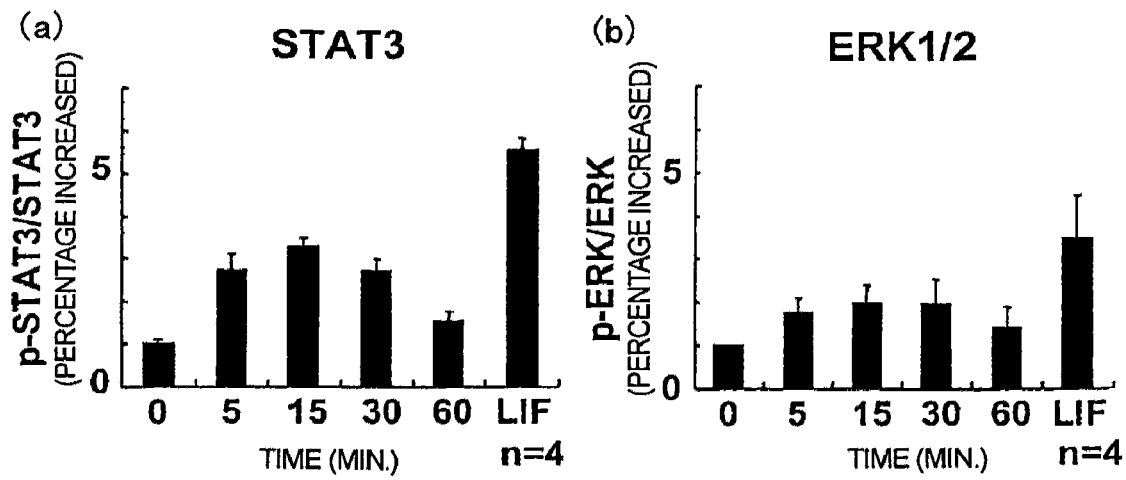
FIGS. 3($a$) and 3($b$) are graphs presenting the results of a Western blot analysis of time-dependent changes in the activation of STAT3 and ERK1/2 in response to IL-11 stimulation; data presented as means±S.E. of four independent experiments; LIF, positive control.
Figure 4:
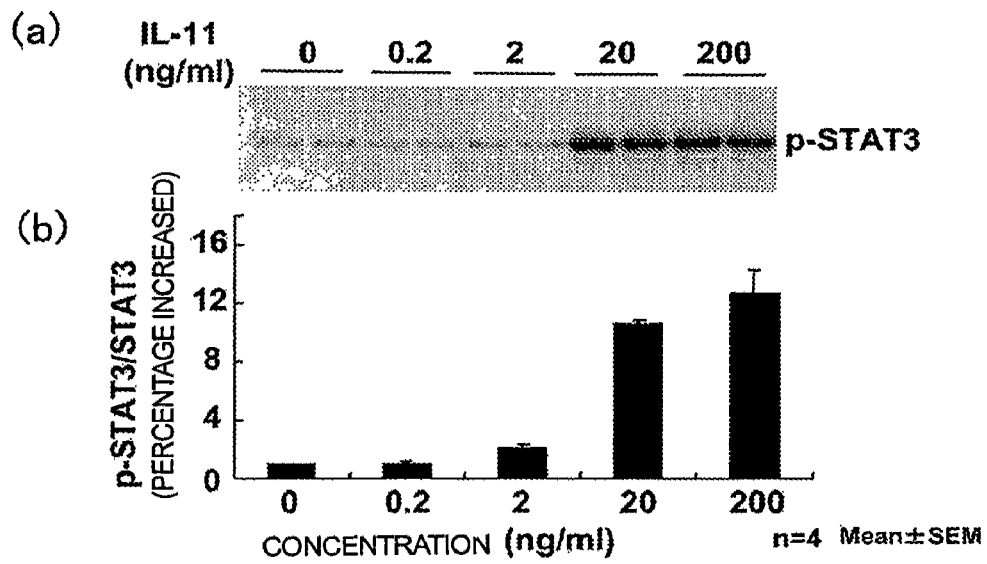
FIGS. 4($a$) and 4($b$) present the results of a Western blot analysis on the IL-11 concentration dependency of STAT3 activation following IL-11 stimulation of cultured cardiomyocytes at varying concentrations; (a) the result of representative immunoblotting; (b) means±S.E. of four independent experiments.

A time course study revealed that STAT3 phosphorylation reaches the peak after 15 minutes from the IL-11 treatment, and gradually attenuates and returns to nearly the original level after 60 minutes. Similar time-dependent changes were noted in ERK1/2, but with smaller magnitudes than in STAT3 (FIG. 3). A study of concentration dependency revealed that STAT3 is maximally phosphorylated at an IL-11 concentration of 20 ng/ml (FIG. 4).

Further, nuclear translocation of phosphorylated STAT3 was observed in cardiomyocytes treated with IL-11. It was also found that IL-11 acts to suppress hydrogen peroxide ($H_2O_2$)-induced cell death through STAT3 activation in cardiomyocytes.

IL-11 Induces Hypertrophy in Cultured Cardiomyocytes

Figure 5:
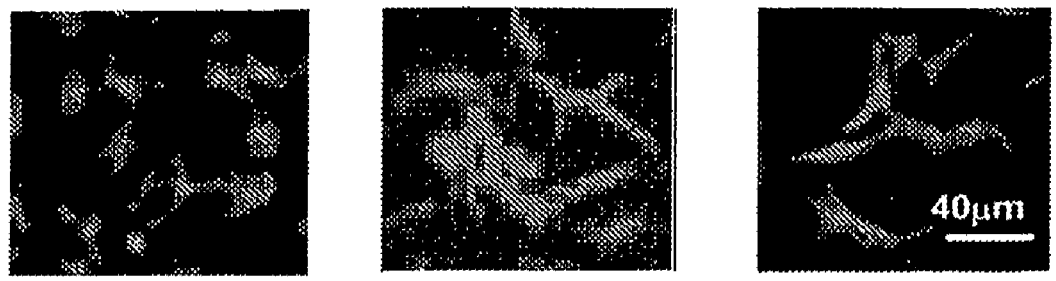
FIGS. 5($a$) through 5($c$) present the results of an evaluation of the morphological influence of IL-11 on cultured cardiomyocytes; (a) cells immunostained with anti-sarcomeric α-actinin antibody after 24-hour IL-11 treatment (20 ng/ml); cont, untreated cells; LIF, positive control ($1\times10^3$ U/ml); (b) cell hypertrophy and extension as quantified by an antibody-positive cell (n=151-227) area; (c) cell hypertrophy and extension as quantified by lengths along the long and short axes; scores, means±S.D.
Figure 5:
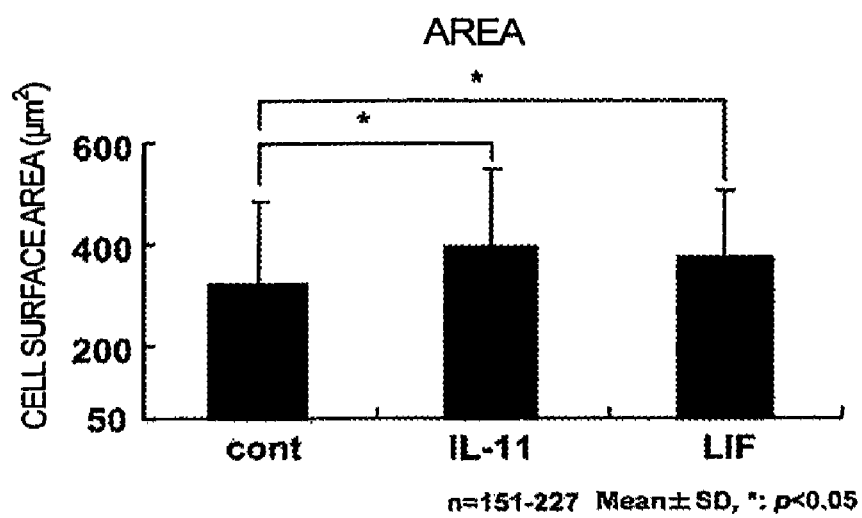
Figure 5:
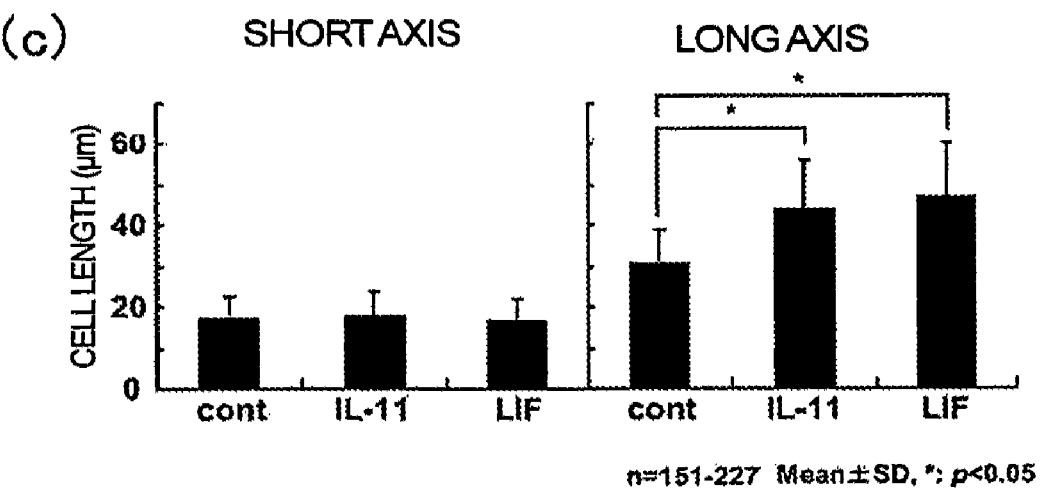

To assess the morphological influence of IL-11 on cultured cardiomyocytes, cells were treated with IL-11 (20 ng/ml) for 24 hours, and immunostained with anti-sarcomeric α-actinin antibody. As a result, hypertrophy with cell elongation was noted in the IL-11-treated cells, as in the positive control (LIF) which underwent a similar morphological change (FIG. 5). The cell hypertrophy and elongation were quantified by measuring the cell area, and the lengths along the long and short axes. There was a significant increase in cell length along the long axis, but no change occurred along the short axis (FIGS. 5(b) and 5(c)).

IL-11 Enhances Viability of Cardiomyocytes

Figure 6:
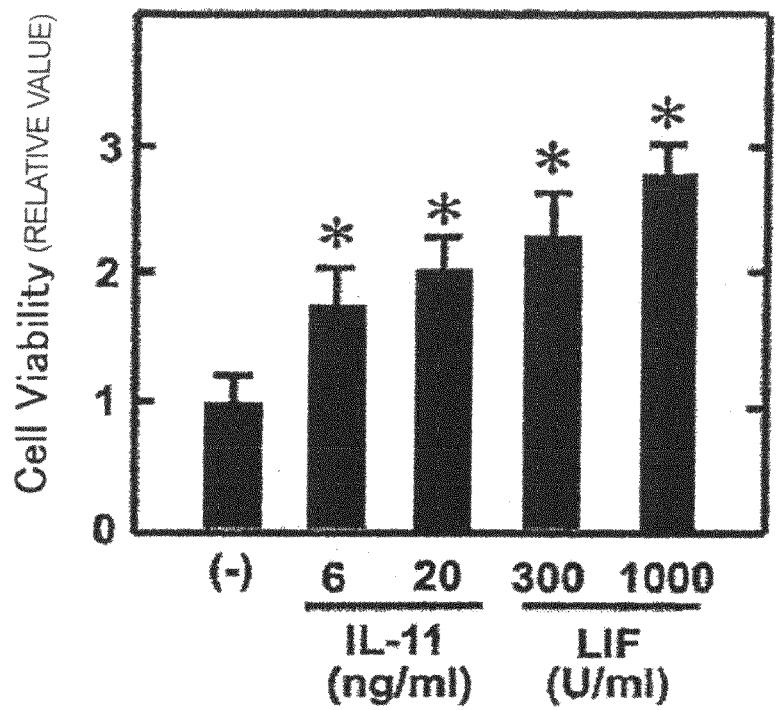
FIG. 6 is a graph presenting the result of an evaluation of cell viability using an MTS (3-(4,5-dimethylthiazole-2-yl)-5-(3-carboxymethoxyphenyl)-2-(4-sulfophenyl)-2H-tetrazolium) assay performed after culturing cardiomyocytes in serum-free medium for 72 hours in the presence or absence of predetermined concentrations of IL-11; LIF, positive control; data presented as means±S.E. of eight experiments under each condition.

A cell viability assay using MTS assay showed about a two-fold increase in MTS metabolic activity in cultured cardiomyocytes treated with IL-11 than in untreated cells (FIG. 6). This result indicates enhancement of cardiomyocyte viability by IL-11.

IL-11 Promotes Vascular Formation In Vivo

Figure 7:
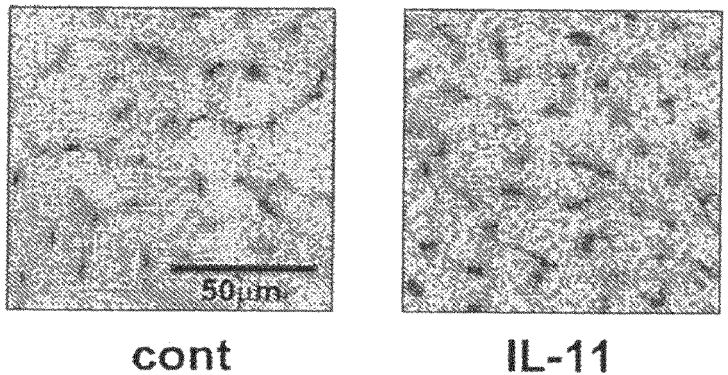
FIGS. 7($a$) and 7($b$) show that IL-11 administration increases the cardiac capillary density in IL-11-treated mice, compared with a control group; (a), a heart slice observed after anti-CD31 antibody immunostaining; (b), quantitative data from multiple mice, means±S.D.
Figure 7:
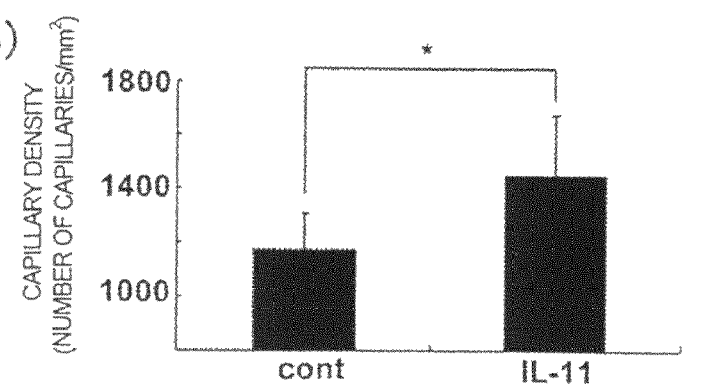

STAT3 activation promotes cardiovascular formation. Mice were repeatedly treated with IL-11 through the tail vein, and changes in capillary density of the heart were observed as a test. IL-11 was given every three days for 5 weeks. The frozen sections were prepared from the heart and immunostained with anti-CD31 antibody to examine capillary density. The capillary density of the heart increased about 1.2 fold in IL-11 administered mice, compared with the control group (FIG. 7). The capillary density started to increase after about 3 weeks from IL-11 administration.

IL-11 Induces VEGF mRNA

Figure 8:
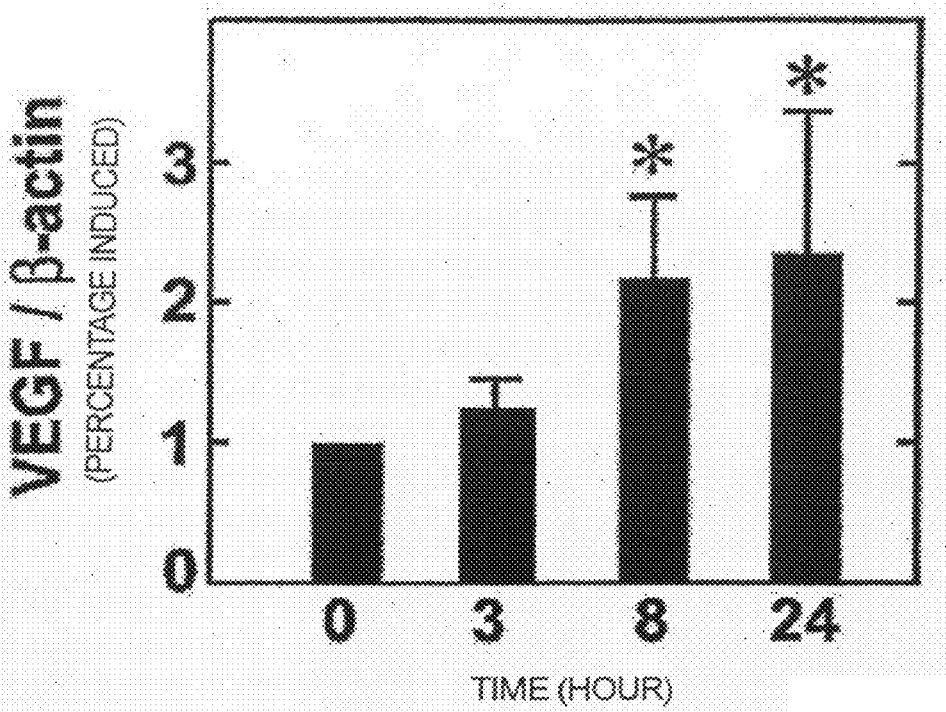
FIG. 8 is a graph presenting the result of a Real-time RT-PCR evaluation of VEGF mRNA expression; the expression level of VEGF mRNA was normalized by that of β-actin mRNA; scores presented as means±S.D. of four to five independent experiments; *, statistical significance against time 0 (hour).

To reveal the mechanism by which IL-11 increases vascular density in vivo, the influence of IL-11 on VEGF mRNA expression was examined in cultured cardiomyocytes using Real-time RT-PCR. VEGF mRNA was significantly upregulated 8 hours after the addition of IL-11, and the expression continued to increase for 24 hours (FIG. 8).

IL-11 Confers the Resistance to Ischemia/Reperfusion Injury on the Heart.

Figure 9:
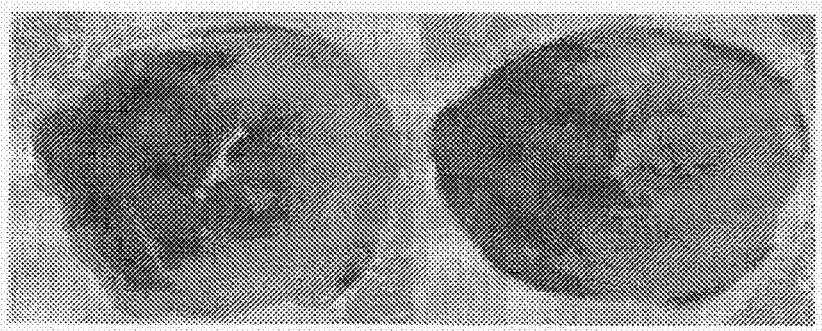
FIGS. 9($a$) and 9($b$) demonstrate the effects of IL-11 on the resistance of the heart to ischemia/reperfusion; (a) an Evans Blue- and TTC-stained heart slice from the mice administered with IL-11 prior to ischemia/reperfusion, shown with the control for comparison; (b) data from multiple mice, means±S.D.
Figure 9:
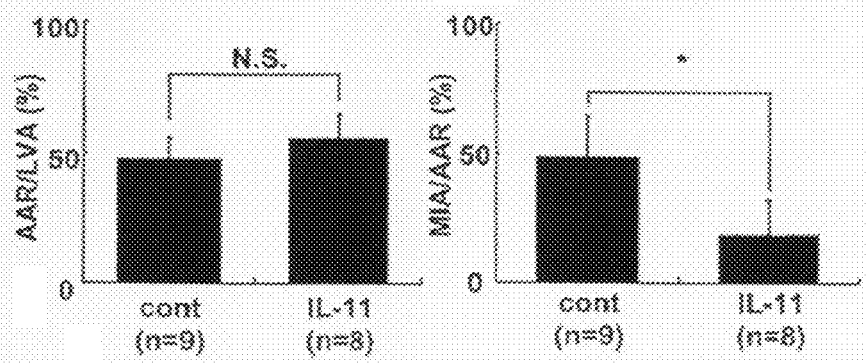

The cardioprotective effect of IL-11 was assessed using a mouse ischemia/reperfusion model. IL-11 or PBS(−) was intravenously administered 18 hours prior to ischemia to prepare an ischemia/reperfusion model, as in the Methods section above. During the course of ischemia/reperfusion, there was no notable change in the heart rate as monitored by ECG. Mortality was 15% or less in the surgery. IL-11 administration had no effect on the risk area, but reduced the infarct size per risk area by 62% (FIG. 9). The result suggests that IL-11 administration renders the cardiac muscle resistant to ischemia/reperfusion.

Efficacy of IL-11 in the Prevention of Onset of Heart Failure After Myocardial Infarction The myocardial protective effect of IL-11 was also evaluated by administrating IL-11 after myocardial injury.

Figure 10:
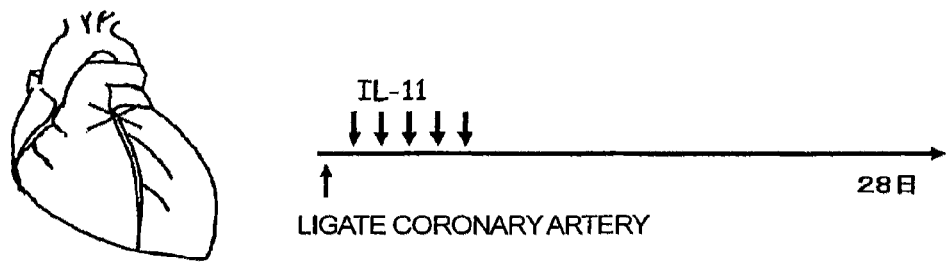
FIG. 10 is a diagram presenting the result of an experiment using myocardial infarction model mice obtained by ligating the coronary artery; X mark, ligation site; the experiment is based on the assessment of fibrosis area in the myocardial tissue of hearts harvested 28 days after the ligation; In IL-11 treated mice, IL-11 was administered on 5 subsequent days one day after coronary ligation; the graph representing means±S.D. of the infarct area (the area of a fibrotic region with respect to the area of the left ventricular myocardium).
Figure 10:
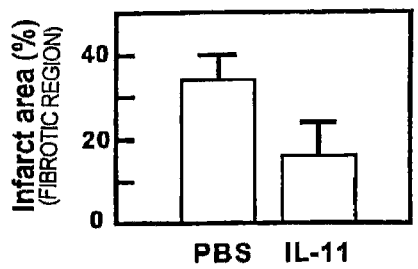

In the experiment, the coronary artery of mice was ligated to produce myocardial infarction (FIG. 10). Twenty-four hours after ligation, IL-11 was administered daily for 5 days through the tail vein (only physiological saline (PBS) for the control). After about one month, the heart was removed from the mouse to assess myocardial fibrosis and intact cardiac muscle.

The result is shown in FIG. 10. Compared with the control group treated with physiological saline (PBS), the infarct area (the proportion of the fibrotic area in the area of the left ventricular myocardium) was remarkably reduced in the IL-11 administered group. As used herein, the term "fibrosis" refers to the state of the myocardial tissue that has lost its contractile elements after infarction. The result suggests that IL-11 functions to repair and/or regenerate the myocardial tissue after infarction.

IL-11 Induces the Reactive Oxygen Species Scavenger Metallothionein, and Cell Protection Factor SPRR (Small Proline Rich Repeated Protein)

Figure 11:
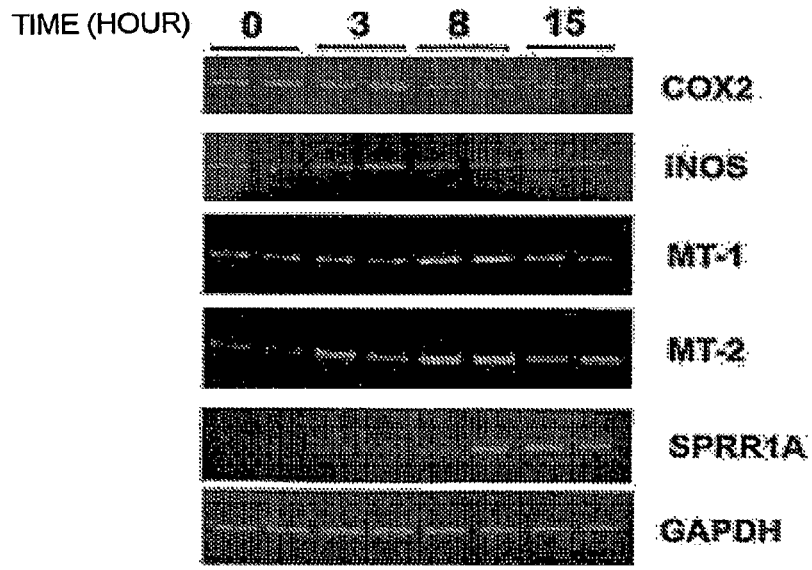
FIG. 11 presents the result of a semi-quantitative RT-PCR analysis evaluating of IL-11-mediated induction of reactive oxygen species scavengers and cell protection factors; IL-11 induced expression of the reactive oxygen species scavenger metallothionein (MT-1, MT-2), and the cell protective gene SPRR (SPRR1A), but did not induce expression of COX2 and iNOS.

Intravenous injection of IL-11 into mice quickly induced expression of the reactive oxygen species scavenger metallothionein (MT-1, MT-2), and a cell protective gene SPRR (SPRR1A) in the heart (FIG. 11). The result suggests that IL-11 induces expression of the reactive oxygen species scavenger and the cell protective gene SPRR, and thereby promotes activation of these cytoprotective molecular pathways in the heart.

IL-11 Administration to Myocardial Infarction Model Mice, and Improvement of Survival Rate Myocardial infarction model mice were created by ligating the coronary artery. IL-11 was administered to the model mice, and its effect on survival rate was evaluated, using PBS administered group, as control.

In the experiment, the coronary artery of mice was ligated to produce myocardial infarction as above. Twenty-four hours after ligation, IL-11 was administered daily for 5 days through the tail vein (only PBS for the control). After administration, the survival rate of each ligated group was compared.

The result is shown in FIG. 12. The IL-11-treated group showed an improved survival rate compared with the control group, demonstrating that IL-11 improves the survival rate after myocardial infarction.

IL-11 Administration to Myocardial Infarction Model Mice, and Repression of Inflammatory Cytokine Expression IL-11 was administered to myocardial infarction-induced mice, and its effect on the expression of cytokines was investigated in the infarct tissues.

In the experiment, the coronary artery of mice was ligated to produce myocardial infarction as above. Twenty-four hours after ligation, IL-11 was administered daily for 5 days through the tail vein (only PBS for the control). Seven days after ligation, the expression level of each cytokine in the infarct tissue was studied using RT-PCR.

The result is shown in FIG. 13. IL-11 administration significantly decreased the expression levels of IL-6 and TNF-α compared with the control group, in which the expression levels of IL-6, IL-1β, and TNF-α were more notable than in the sham surgery group that had no ligation. Since IL-6 and TNF-α are known as proinflammatory cytokines, the result confirmed that IL-11 exhibits anti-inflammatory action in the infarct tissue by repressing (inhibiting) expression of the inflammatory cytokines after myocardial infarction.

On the other hand, IL-11 administration did not have any significant effects on the expression level of IL-1β, which has cardiomyocyte protective effect, compared with the control group.

INDUSTRIAL APPLICABILITY

As described above, the present invention demonstrates the myocardial protective effect of interleukin 11 in vivo, and provides a preventive or a therapeutic drug for heart disease etc. using interleukin 11 as the active ingredient. The invention is applicable to ordinary pharmaceutical preparations, or can be used to provide food products, such as health food and food supplements, that have a heart disease preventing action.

The invention claimed is:

1. A method of treating heart disease, consisting of administering an effective amount of interleukin 11 (IL-11) and a carrier or vehicle to a patient in need thereof, wherein the heart disease is selected from the group consisting of myocardial remodeling after a myocardial injury and myocardial infarction, wherein the administration of the IL-11 regenerates myocardial tissue.

2. The method according to claim 1, wherein the heart disease is myocardial remodeling after a myocardial injury.

3. The method according to claim 1, wherein the heart disease is myocardial infarction.

* * * * *

```
                        SEQUENCE LISTING

<160> NUMBER OF SEQ ID NOS: 17

<210> SEQ ID NO 1
<211> LENGTH: 20
<212> TYPE: DNA
<213> ORGANISM: Artificial
<220> FEATURE:
<223> OTHER INFORMATION: Primer

<400> SEQUENCE: 1
gtgtcctggt ttcgggatgg                                                  20

<210> SEQ ID NO 2
<211> LENGTH: 20
<212> TYPE: DNA
<213> ORGANISM: Artificial
<220> FEATURE:
<223> OTHER INFORMATION: Primer

<400> SEQUENCE: 2
tccaggtgcc agcatccaga                                                  20

<210> SEQ ID NO 3
<211> LENGTH: 25
<212> TYPE: DNA
<213> ORGANISM: Artificial
<220> FEATURE:
<223> OTHER INFORMATION: Primer

<400> SEQUENCE: 3
gacaggatgc agaaggagat tactg                                            25

<210> SEQ ID NO 4
<211> LENGTH: 21
<212> TYPE: DNA
<213> ORGANISM: Artificial
<220> FEATURE:
<223> OTHER INFORMATION: Primer

<400> SEQUENCE: 4
agagccacca atccacacag a                                                21

<210> SEQ ID NO 5
<211> LENGTH: 29
<212> TYPE: DNA
<213> ORGANISM: Artificial
<220> FEATURE:
<223> OTHER INFORMATION: Probe
```

```
<400> SEQUENCE: 5
aagatcattg ctcctcctga gcgcaagta                                29

<210> SEQ ID NO 6
<211> LENGTH: 29
<212> TYPE: DNA
<213> ORGANISM: Artificial
<220> FEATURE:
<223> OTHER INFORMATION: Primer

<400> SEQUENCE: 6
ggtctggtgc ctggtctgat gatgtatgc                                29

<210> SEQ ID NO 7
<211> LENGTH: 30
<212> TYPE: DNA
<213> ORGANISM: Artificial
<220> FEATURE:
<223> OTHER INFORMATION: Primer

<400> SEQUENCE: 7
gggggtgcca gtgatagagt gtgttgaatt                               30

<210> SEQ ID NO 8
<211> LENGTH: 24
<212> TYPE: DNA
<213> ORGANISM: Artificial
<220> FEATURE:
<223> OTHER INFORMATION: Primer

<400> SEQUENCE: 8
tgaagccccg ctactactcc atca                                     24

<210> SEQ ID NO 9
<211> LENGTH: 22
<212> TYPE: DNA
<213> ORGANISM: Artificial
<220> FEATURE:
<223> OTHER INFORMATION: Primer

<400> SEQUENCE: 9
ttgcggacca tctcctgcat tt                                       22

<210> SEQ ID NO 10
<211> LENGTH: 25
<212> TYPE: DNA
<213> ORGANISM: Artificial
<220> FEATURE:
<223> OTHER INFORMATION: Primer

<400> SEQUENCE: 10
cgtagctcca gcttcaccag atctc                                    25

<210> SEQ ID NO 11
<211> LENGTH: 19
<212> TYPE: DNA
<213> ORGANISM: Artificial
<220> FEATURE:
<223> OTHER INFORMATION: Primer

<400> SEQUENCE: 11
tggtggcagc gctgttcgt                                           19
```

```
<210> SEQ ID NO 12
<211> LENGTH: 23
<212> TYPE: DNA
<213> ORGANISM: Artificial
<220> FEATURE:
<223> OTHER INFORMATION: Primer

<400> SEQUENCE: 12
accgatctct cgtcgatctt caa                                              23

<210> SEQ ID NO 13
<211> LENGTH: 30
<212> TYPE: DNA
<213> ORGANISM: Artificial
<220> FEATURE:
<223> OTHER INFORMATION: Primer

<400> SEQUENCE: 13
gcttctacat ggtctattta cacagatgtg                                       30

<210> SEQ ID NO 14
<211> LENGTH: 23
<212> TYPE: DNA
<213> ORGANISM: Artificial
<220> FEATURE:
<223> OTHER INFORMATION: Primer

<400> SEQUENCE: 14
ggaccaagtg ctatctaacc atg                                              23

<210> SEQ ID NO 15
<211> LENGTH: 23
<212> TYPE: DNA
<213> ORGANISM: Artificial
<220> FEATURE:
<223> OTHER INFORMATION: Primer

<400> SEQUENCE: 15
ggtcttcagg catggctctg gac                                              23

<210> SEQ ID NO 16
<211> LENGTH: 21
<212> TYPE: DNA
<213> ORGANISM: Artificial
<220> FEATURE:
<223> OTHER INFORMATION: Primer

<400> SEQUENCE: 16
catcaccatc ttccaggagc g                                                21

<210> SEQ ID NO 17
<211> LENGTH: 21
<212> TYPE: DNA
<213> ORGANISM: Artificial
<220> FEATURE:
<223> OTHER INFORMATION: Primer

<400> SEQUENCE: 17
gaggggccat ccacagtctt c                                                21
```